(12) United States Patent
Dixon

(10) Patent No.: US 9,770,561 B1
(45) Date of Patent: Sep. 26, 2017

(54) DEVICE FOR GIVING INJECTIONS

(71) Applicant: Freddie Larren Dixon, Stow, OH (US)

(72) Inventor: Freddie Larren Dixon, Stow, OH (US)

(*) Notice: Subject to any disclaimer, the term of this patent is extended or adjusted under 35 U.S.C. 154(b) by 0 days.

(21) Appl. No.: 15/081,139

(22) Filed: Mar. 25, 2016

(51) Int. Cl.
*A61M 5/42* (2006.01)
*A61B 5/15* (2006.01)

(52) U.S. Cl.
CPC ....... *A61M 5/422* (2013.01); *A61B 5/150106* (2013.01); *A61B 5/150137* (2013.01); *A61M 2205/59* (2013.01); *A61M 2205/8206* (2013.01)

(58) Field of Classification Search
CPC ............. A61M 5/422; A61B 5/150106; A61B 5/150137
See application file for complete search history.

(56) References Cited

U.S. PATENT DOCUMENTS

| | | | |
|---|---|---|---|
| 3,620,209 A | 11/1971 | Kravitz | |
| 5,578,014 A | 11/1996 | Erez et al. | |
| 5,647,851 A | 7/1997 | Pokras | |
| 6,231,531 B1 | 5/2001 | Lum et al. | |
| 6,620,133 B1 | 9/2003 | Steck | |
| 7,740,632 B2 | 6/2010 | Young | |
| 8,469,918 B2 * | 6/2013 | Fallek | B65D 25/24 433/118 |
| 2002/0082564 A1 | 6/2002 | Pham | |
| 2004/0267299 A1 * | 12/2004 | Kuriger | A61B 5/15186 606/181 |
| 2005/0177071 A1 | 8/2005 | Nakayama et al. | |
| 2006/0100656 A1 | 5/2006 | Olson et al. | |

* cited by examiner

*Primary Examiner* — Nathan R Price
*Assistant Examiner* — Courtney Fredrickson
(74) *Attorney, Agent, or Firm* — L. R. Drayer

(57) ABSTRACT

A device for giving injections has a housing having a lower surface and an upper surface with a passage through the housing extending between the upper and lower surfaces. A DC motor with an eccentric fixed to the motor is located inside the housing to vibrate the housing. At least one tubular insert is located in the passage through the housing and is fixed to the housing. A syringe receiver is located inside and fixed to the at least one tubular insert. The syringe receiver contains a foam insert defining a space for receiving a syringe. The foam insert is a polyurethane foam characterized by an indentation force deflection of about 25% at 127 N and about 65% at 256N. The foam insert isolates a syringe from the vibrating of the housing.

3 Claims, 13 Drawing Sheets

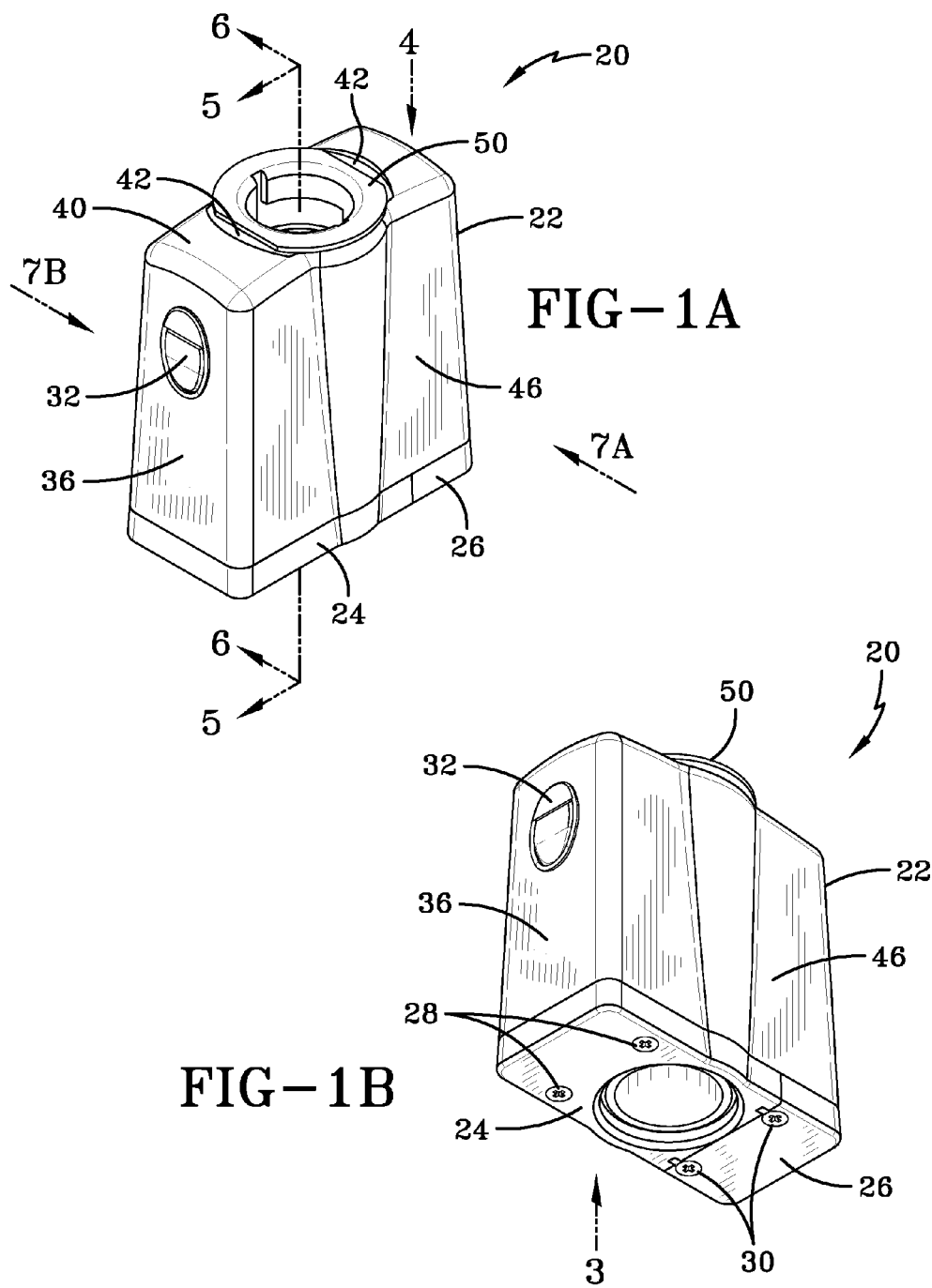

DEVICE FOR GIVING INJECTIONS

FIELD OF THE INVENTION

The present invention relates to a device that assists in giving injections to a person.

BACKGROUND OF THE INVENTION

There are many devices that are used for aiding the delivery of medicine from a syringe to an injection site on a patient. One problem is the inexperience of caregivers that are not medical professionals who must give injections to children such as insulin injections to a young child with diabetes. The child may have a well founded natural anxiety of pain from injections. The caregiver may be nervous about causing the child pain and about giving an injection properly. The present invention provides a device that both distracts the child and aids the caregiver in giving an injection properly.

DISCUSSION OF THE PRIOR ART

U.S. Pat. No. 3,620,209 teaches a device that is strapped on a patient's limb with a vibrating horseshoe shaped member. A caregiver may give an injection freehand with an unstabilized syringe and needle into the skin bordered by the vibrating horseshoe. The use of the device is limited to a patent's limb because of the need to strap the device in place; however insulin injections are often given on the abdomen, hips or upper thigh so the disclosed device is not suitable.

U.S. Pat. No. 5,578,014 teaches an injection device that employs a cooling device with a cold plate that surrounds the injection site to numb the skin. A needle protrudes through an opening in the cold plate to deliver an injection.

U.S. Pat. No. 5,647,851 teaches a motorized injection device that causes a needle to vibrate during injection of Novocain for a dental procedure.

U.S. Pat. No. 6,231,531 B1 teaches a device that causes a patient some degree of pain using a vibrating needle to distract the patient's attention from a procedure, such as blood sampling, being performed at a different location.

US 2002/0082564 A1 teaches a toy used as a syringe holder to camouflage the syringe from a patient that is afraid of needles.

U.S. Pat. No. 6,602,229 teaches a device that is clamped onto a syringe to cause the syringe and needle to vibrate.

US 2005/0177071 A1 teaches a spring loaded lancet that protrudes through an opening in a vibrating surface. There is no suggestion that the lancet should be isolated from the vibration.

US 2006/0100656 A1 teaches a depth adjustment mechanism to control the depth of penetration of a needle or lance.

U.S. Pat. No. 7,740,632 B2 teaches a device for delivering a viscous material such as bone cement from a syringe provided with a vibrator to increase the tendency of the viscous material to flow making delivery into the body of such materials easier and more

SUMMARY OF THE INVENTION

A device for giving injections includes a housing having a lower surface and an upper surface with a passage through the housing extending between the upper and lower surfaces. A DC motor with an eccentric fixed to the motor is located inside the housing to vibrate the housing. At least one tubular insert is located in the passage through the housing and is fixed to the housing. A syringe receiver is located inside and fixed to the at least one tubular insert with the syringe receiver containing a foam insert defining a space for receiving a syringe. The foam insert is a polyurethane foam characterized by an indentation force deflection of about 25% at 127 N and about 65% at 256N. The foam insert isolates a syringe from the vibrating of the housing.

BRIEF DESCRIPTION OF THE DRAWINGS

FIG. 1A is a top perspective view of an exemplary device of the present invention for assisting in giving injections.

FIG. 1B is a bottom perspective view of the exemplary device.

FIG. 2A is a first side elevation view of the exemplary device.

FIG. 2B is a second side elevation view of the exemplary device showing a

DETAILED DESCRIPTION OF THE INVENTION

Figures 2A, 2B:
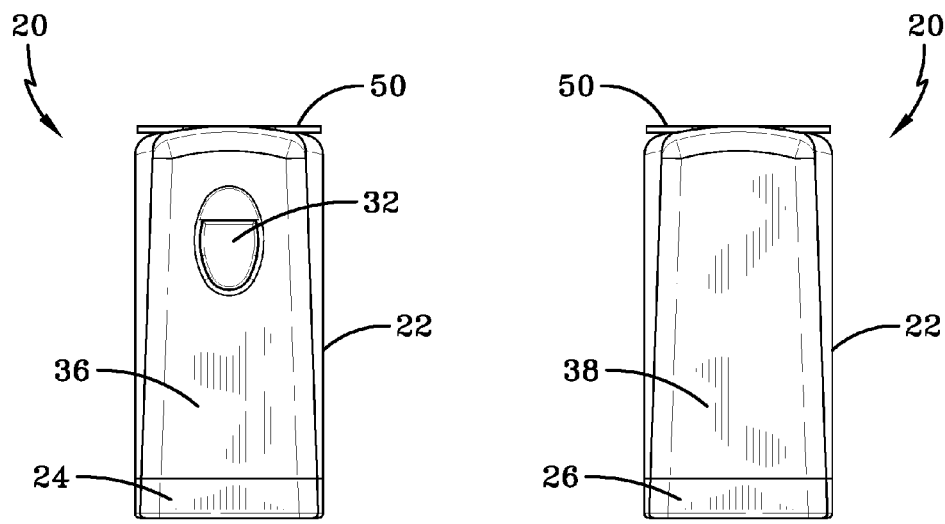
Figure 3:
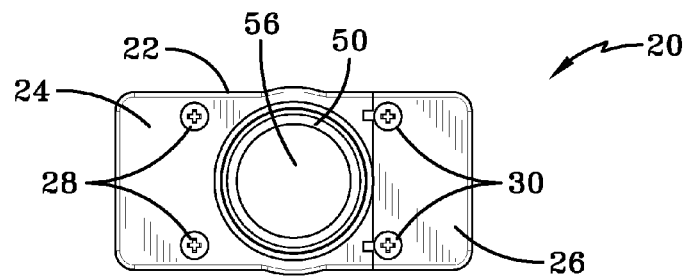
FIG. 3 is a bottom view of the exemplary device.
Figure 4:
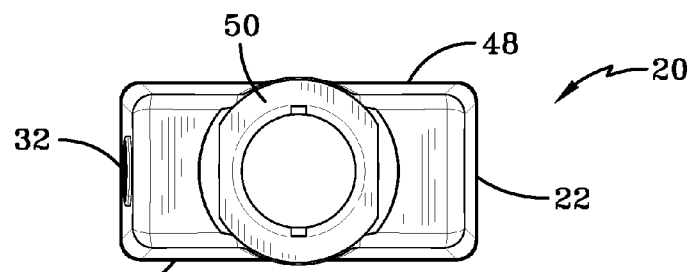
FIG. 4 is a top view of the exemplary device.

FIGS. 1A-4 show the exterior on an exemplary device 20 of the present invention for assisting in giving injections to a person. FIG. 1A is a top perspective view of the exemplary device; FIG. 1B is a bottom perspective view of the exemplary device; FIG. 2A is a first side elevation view of the exemplary device; FIG. 2B is a second side elevation view of the exemplary looking showing a side of the device opposite the side shown in FIG. 2A; FIG. 3 is a bottom view of the exemplary; and FIG. 4 is a top view of the exemplary device.

A side of a device 20 defined by a housing cover 24 and a battery compartment cover 26, as best shown in FIGS. 1A, 1B and 3, is intended to be adjacent to the skin of a person when a device of the present invention is used for giving injections. As used herein and in the claims when referring to the device of the present invention terms such as "above", "below", "higher", "lower" and similar terms defining locations are understood to relate to the device when a side of the device defined by the housing cover 24 and the battery compartment cover 26 rest on a horizontal surface with the device extending upward from the horizontal surface.

A housing body 22 has two pairs of opposed sidewalls 36, 38; 46, 48 and one end wall 40, with an opposing end of the housing body having openings for receiving various components of the device in a manner to be described later. A housing body cover 24 is fastened to the open end, which is the lower end, of the housing body 22 by a suitable means for fastening such as screws 28. A battery compartment cover 26 is fastened to the open end, which is the lower end, of the housing body 22 by a suitable means for fastening such as screws 30. Other suitable means for fastening the housing body cover 24 and battery compartment cover 26 to the housing body 22 include clips, tongue and groove arrangements and snap fit arrangements. While it is envisioned that the housing body, housing body cover and battery compartment cover may comprise a suitable molded polymer material, it is understood that these components of the device may comprise any suitable material selected in accordance with good engineering practice.

Figure 7A:
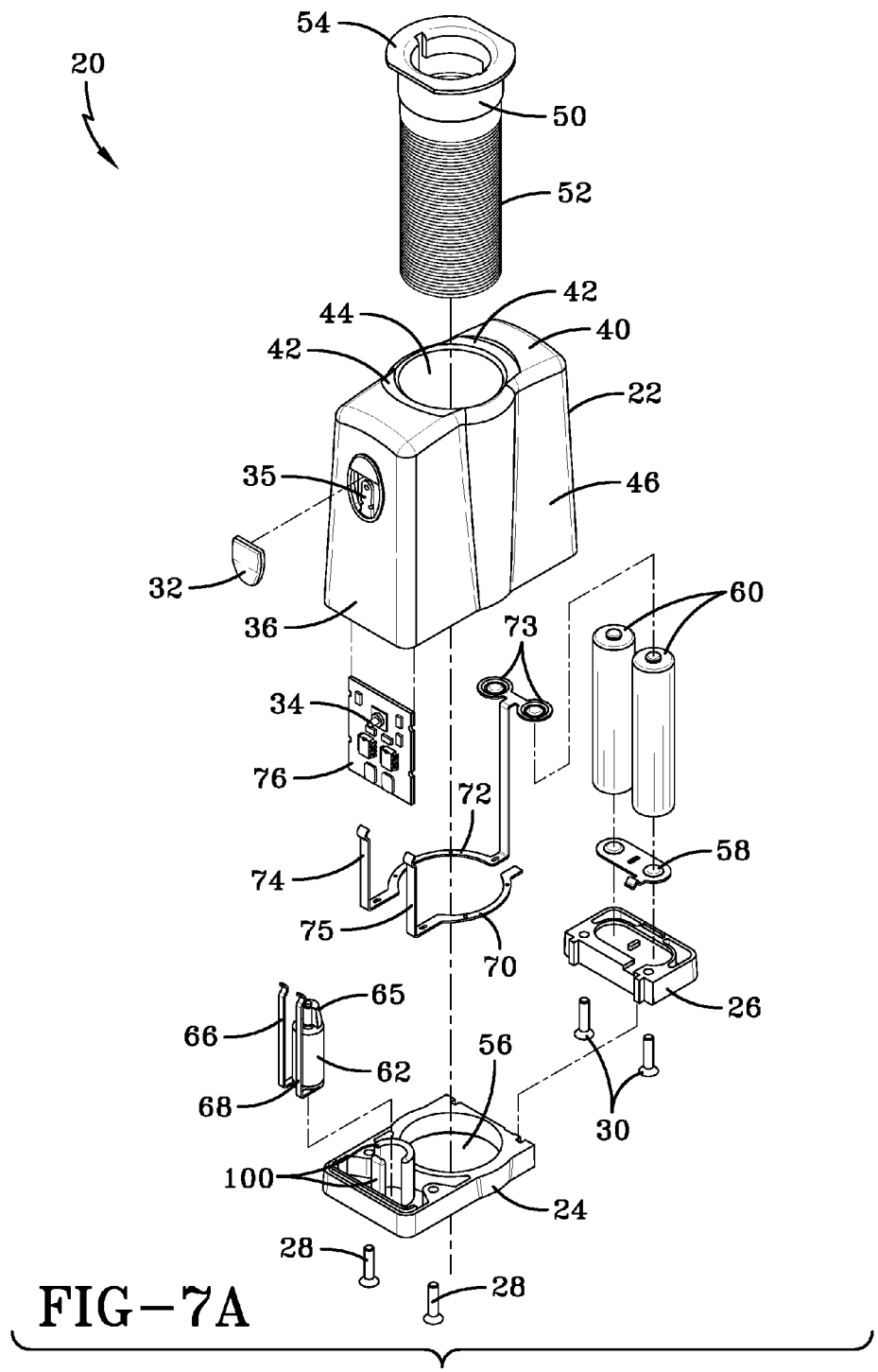
FIG. 7A is a first perspective exploded view of the exemplary device looking in a first direction.

An on/off switch 32 is located on a sidewall 36 of the housing body 22. As best shown in FIG. 7A the closed end 40 of the housing body 22 has a circular opening 44 that is surrounded by a ledge 42. A threaded tubular insert 50 is inserted into the circular opening 44 as shown in FIGS. 1A and 4. Referring to FIGS. 1 B and 3 a lower end of the threaded tubular insert 50 is viewable through an opening 56 in the housing body cover 24 on the lower end of the device 20.

Figure 4A:
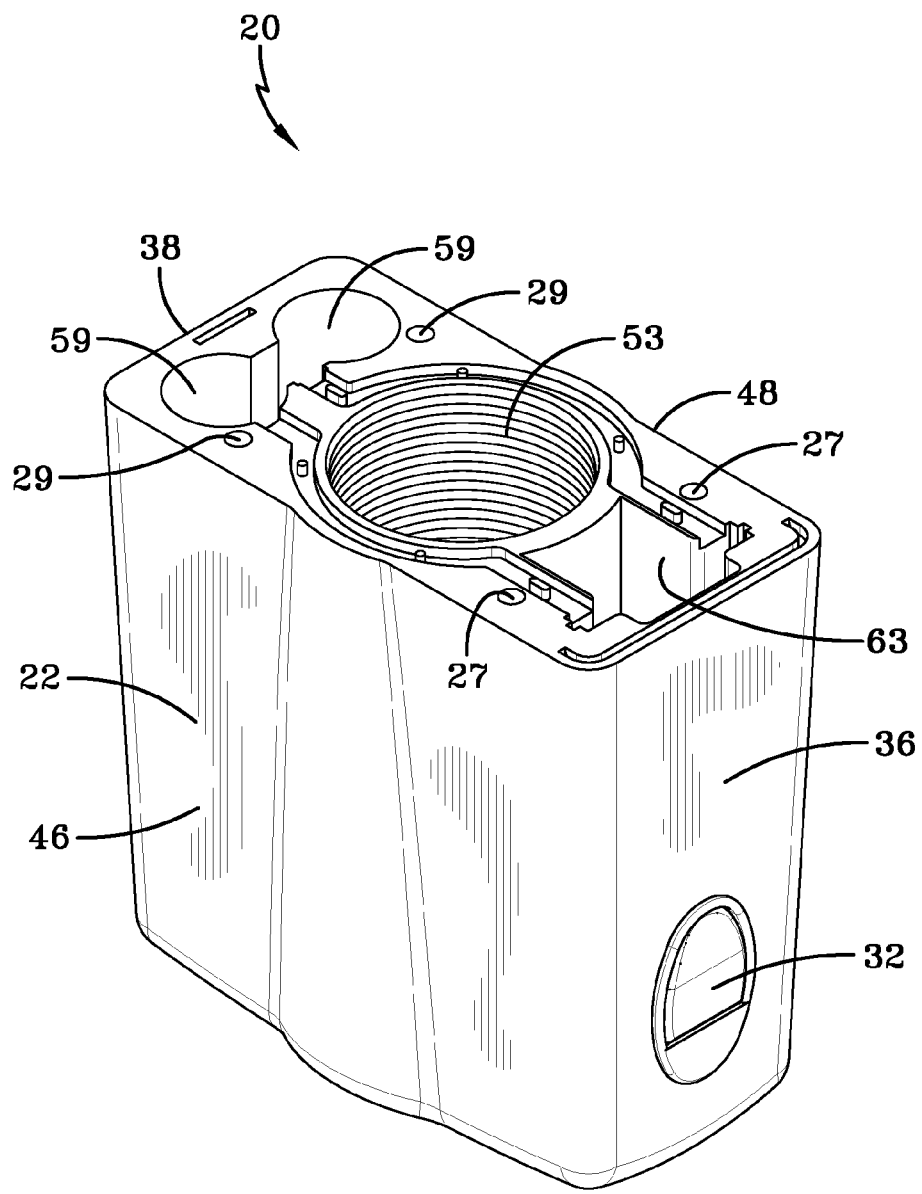
FIG. 4A is a bottom perspective view of the exemplary device with the end cover plat and battery compartment cover removed.

FIG. 4A is a bottom perspective view of the exemplary device 20 with the end cover plate and battery compartment cover removed and without the batteries, electrical components and threaded tubular insert. The housing 22 is molded and configured to have compartments 59 for receiving batteries and a compartment 63 for receiving electrical components of the device. The lower side of the housing is provided with holes 27, 29 for receiving threaded fasteners and with features to aid in aligning the placement of the housing body cover and battery compartment cover with respect to the lower side of the housing. Because the threaded tubular insert is not shown in FIG. 4A the threads 53 on interior wall of well that receives the threaded tubular insert are visible.

Figure 5:
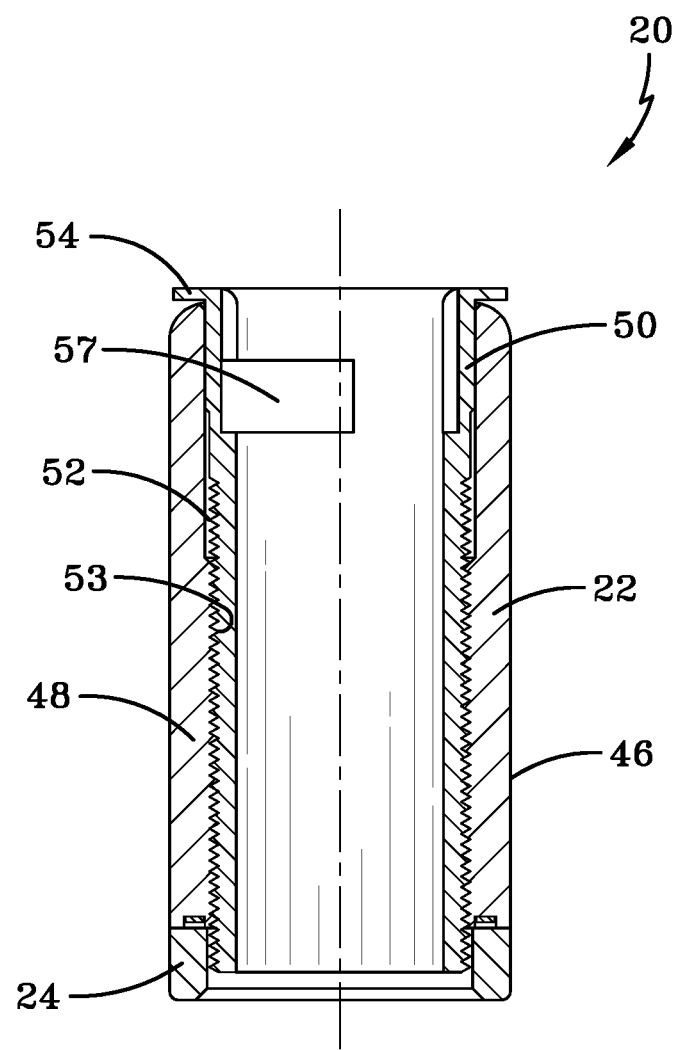
FIG. 5 is a section view of the exemplary device taken at line 5-5 of FIG. 1A.
Figure 6:
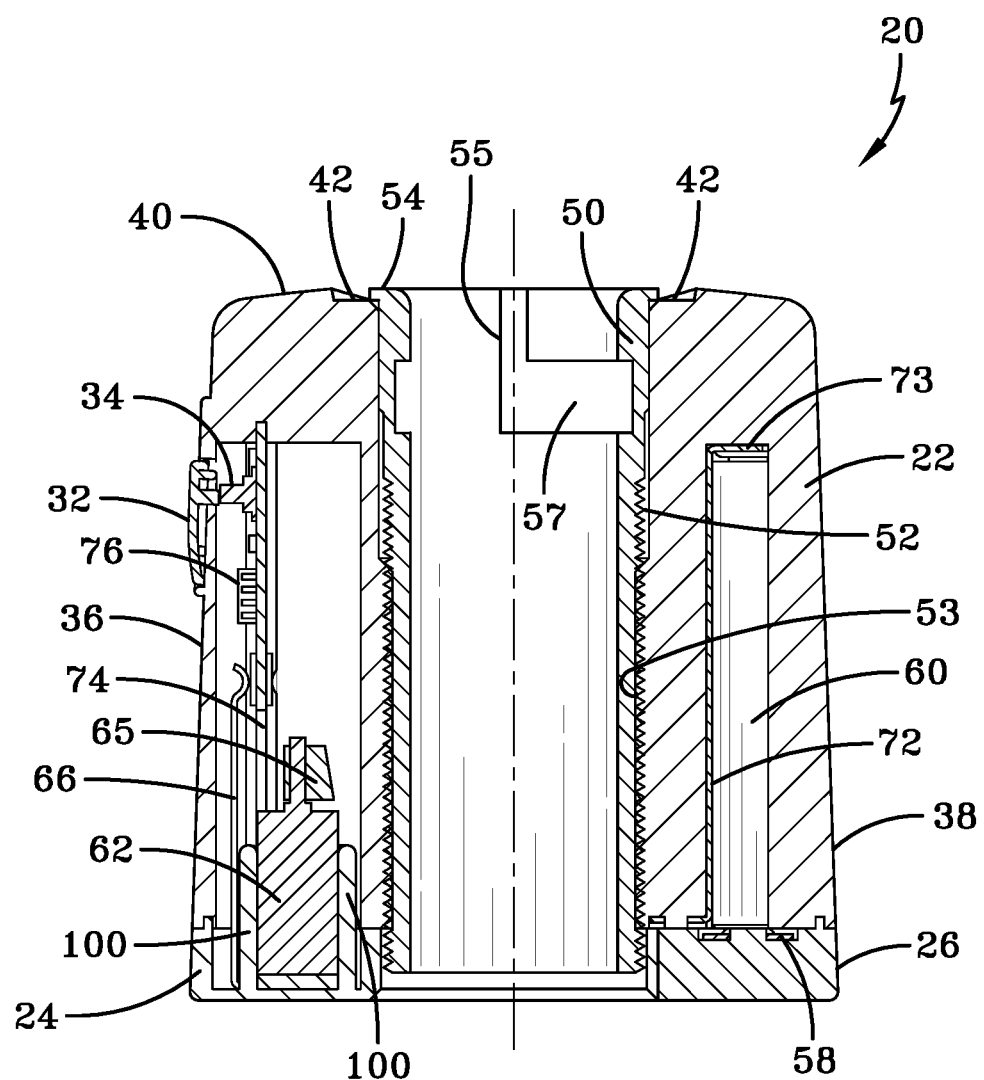
FIG. 6 is a section view of the exemplary device taken at line 6-6 of FIG. 1A.
Figure 7B:
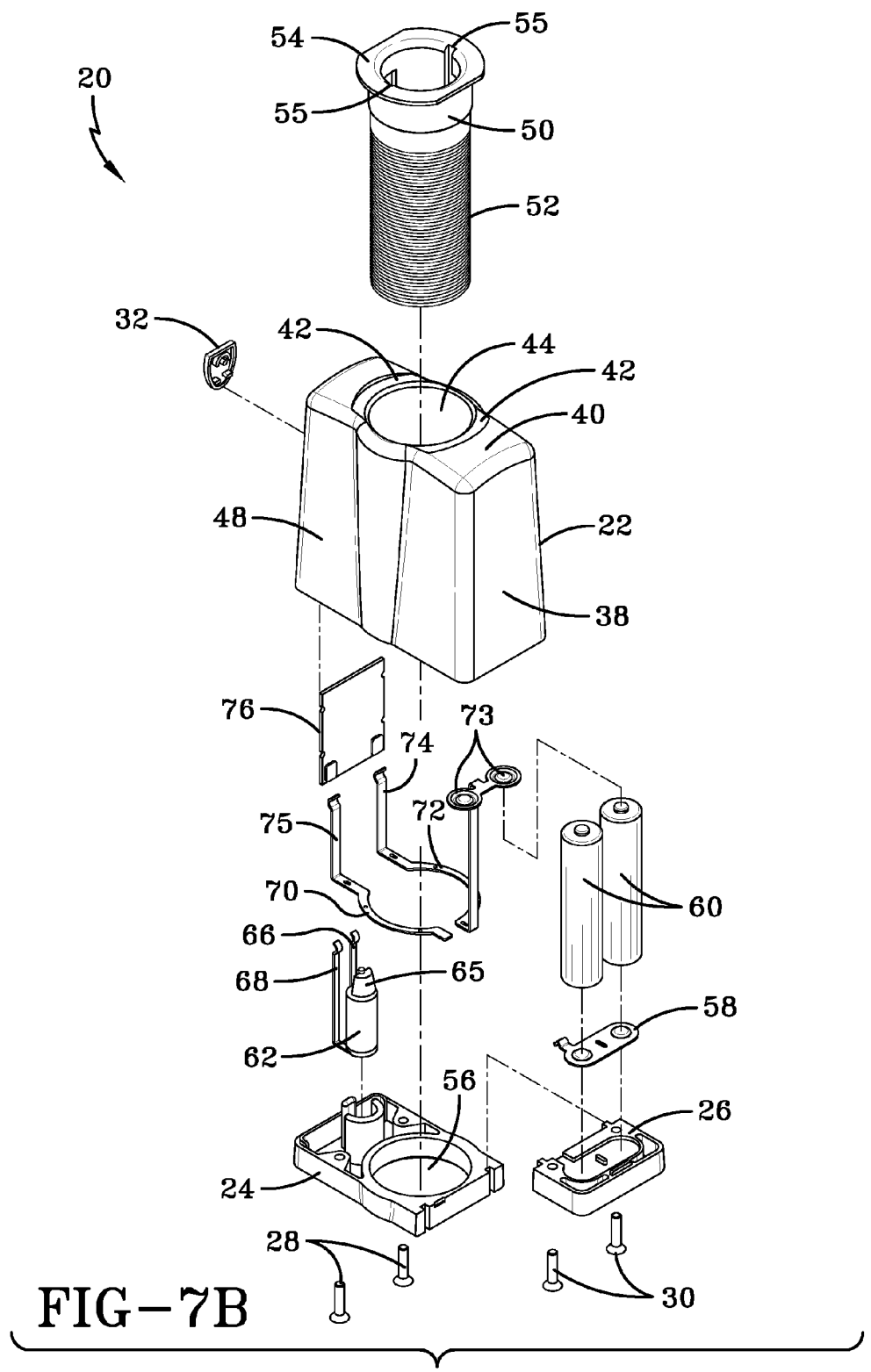
FIG. 7B is a second perspective exploded view of the exemplary device of looking in a second direction that is opposite to the first direction.
Figure 11:
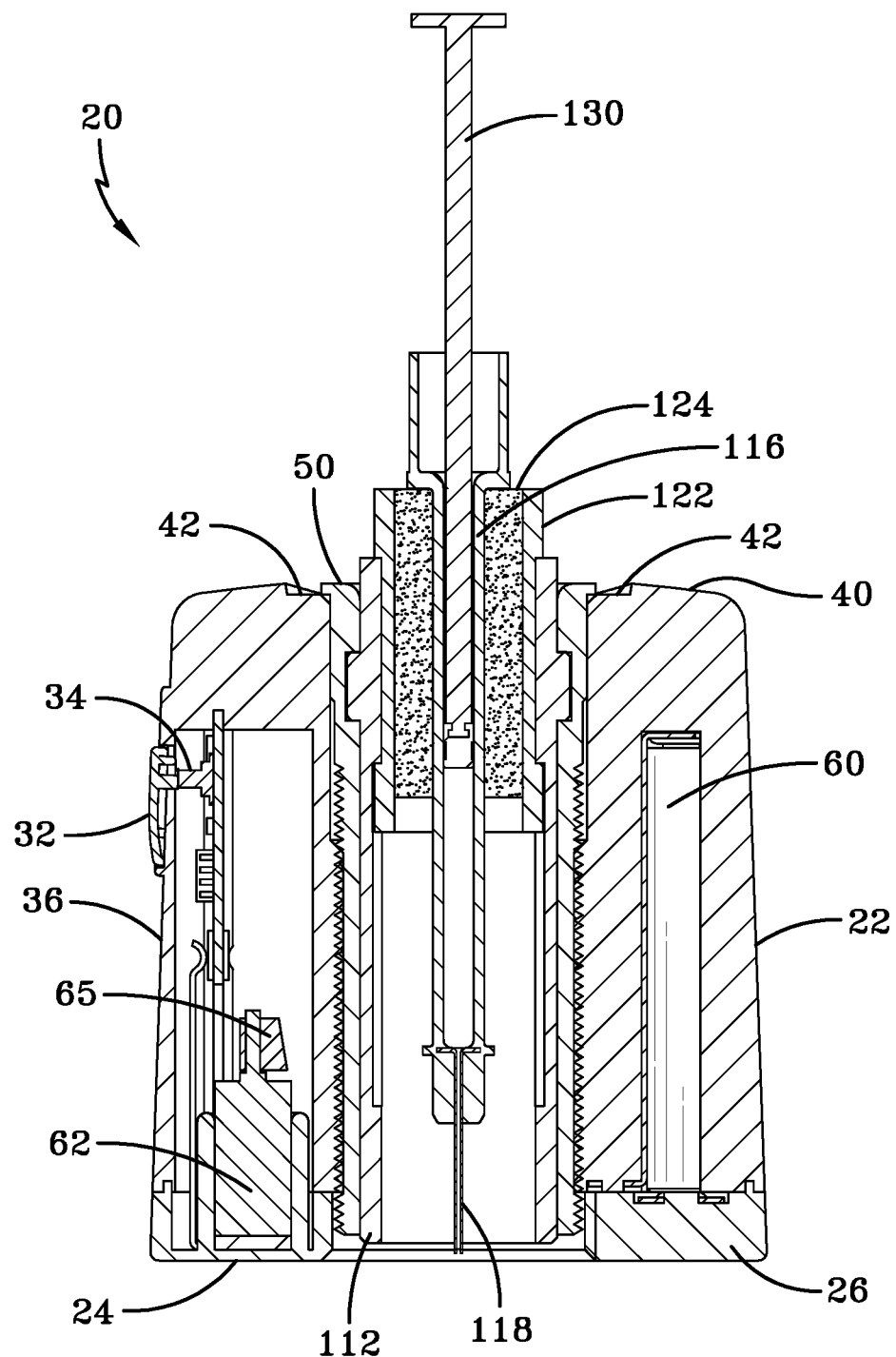
FIG. 11 is a section view of the exemplary device taken at line 11-11 of FIG. 8.

The structure, function and location of various components of the device 20 inside the housing 22 can best be understood by referring to FIGS. 5-7B and 11 in unison. FIG. 5 is a first section view of the exemplary device taken at line 5-5 of FIG. 1A with the electrical and mechanical components in their operative configuration. FIG. 6 is a second section view oriented perpendicular the first section view taken at line 6-6 FIG. 1A with the electrical and mechanical components in their operative configuration. FIG. 11 is a larger section view of the exemplary device taken at line 11-11 of FIG. 9 with the electrical and mechanical components in their operative configuration. FIG. 7A is a first perspective exploded view of the exemplary device looking in a first direction, and FIG. 7B is a second perspective exploded view of the exemplary device of looking in a second direction that is opposite to the first direction.

A threaded tubular insert 50 that may be a molded plastic piece that has a flange 54 at one end that limits the depth the tubular insert may be inserted into the housing 22 and can be grasped for turning the tubular insert during assembly with the housing. Threads 52 on the exterior of the threaded tubular insert mate with threads 53 on interior wall of well in the housing 22. As will be explained later the location of the threaded tubular insert in the housing is variable using the threads to accommodate needles and syringes of various sizes and the depth of penetration of a needle into the flesh of a patient. A vertical groove 55 in an interior wall of the threaded tubular insert intersects a circumferentially extending groove 57 in the interior wall of the threaded tubular insert to accommodate interlocking of a sleeve for a syringe in a manner that will be described later.

The battery compartment cover 26 supports a battery contact member 58. A first conductor 72 is provided with another battery contact member 73. Two batteries 60 (for example AA or AAA cells) are in conductive communication with the battery contact members 58, 73 in a conventional manner. The battery contact 73, the batteries 60 and a portion of the first conductor 72 are located in the compartments 59.

An upper side of the housing body cover 24 on the lower end of the device 20 has upwardly extending curved projections 100. A small DC motor 62 is fixed to second and third conductors 66, 68. The second and third conductors 66, 68 are in conductive contact with a circuit board 76. An eccentric weight 65 is attached to the DC motor 62 to cause vibration. As best seen in FIGS. 6 and 11 the DC motor 62 is snuggly nested in a space between the upwardly extending curved projections 100 of the housing body cover 24. A vertical portion 74 of the first conductor 72 is in conductive contact with the circuit board 76. A vertical portion 75 of a fourth conductor 70 is in conductive contact with the circuit board 76. The 70 conductor is also in conductive contact with the battery contact member 58 to complete the circuit that causes the DC electric motor 62 to operate and vibrate. When the DC electric motor 62 operates and vibrates the vibration is imparted to the housing body cover 24 and the battery cover 26 which are fixed to the lower end of the housing 22. The degree of vibration is greatest in the housing body cover 24 and the battery cover 26 and dissipates to a lower degree of vibration of the housing 22 as the distance from the housing body cover 24 and the battery cover 26 increases. It is to be noted that the lower surfaces of the housing body cover 24 and the battery cover 26 are the portion of the device that contact the skin of a person when the device is used to give an injection to the person.

The plastic on and off switch 32 is fixed to a first switch contact 35 that engages and disengages a second switch contact 34 attached to the circuit board 76 to turn the DC electric motor on and off.

Figure 8:
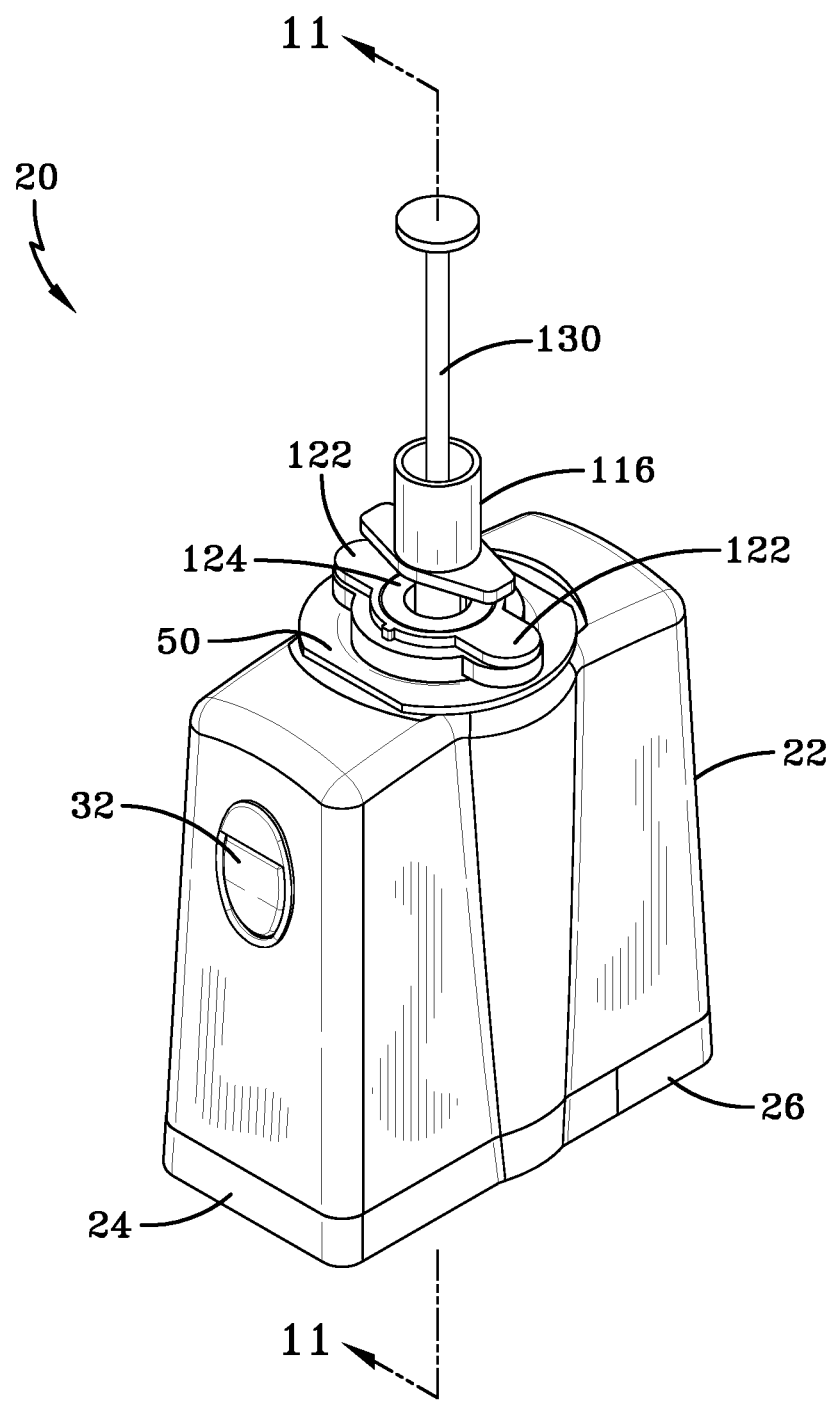
FIG. 8 is a top perspective view of the exemplary device in combination with a syringe used for giving an injection.
Figure 9:
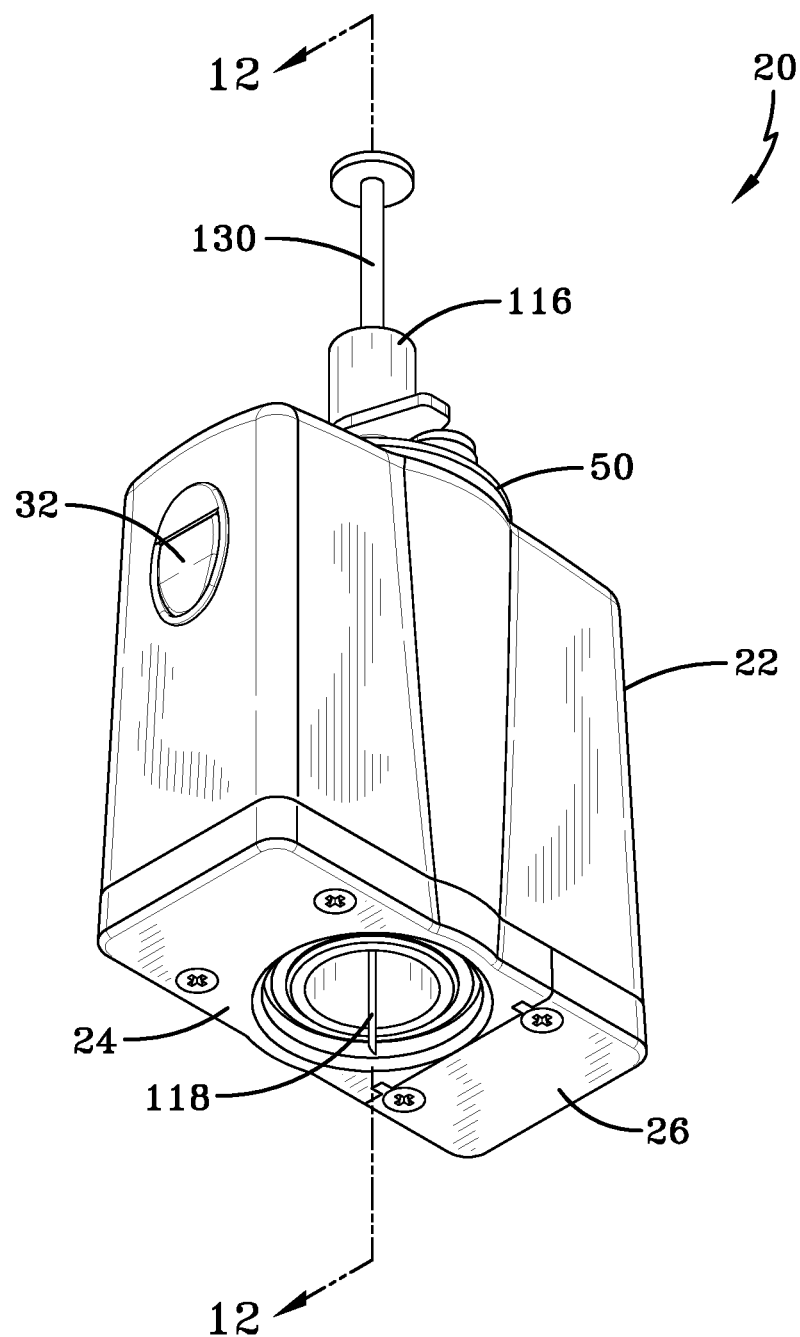
FIG. 9 is a bottom perspective view of the exemplary device in combination
Figure 10:
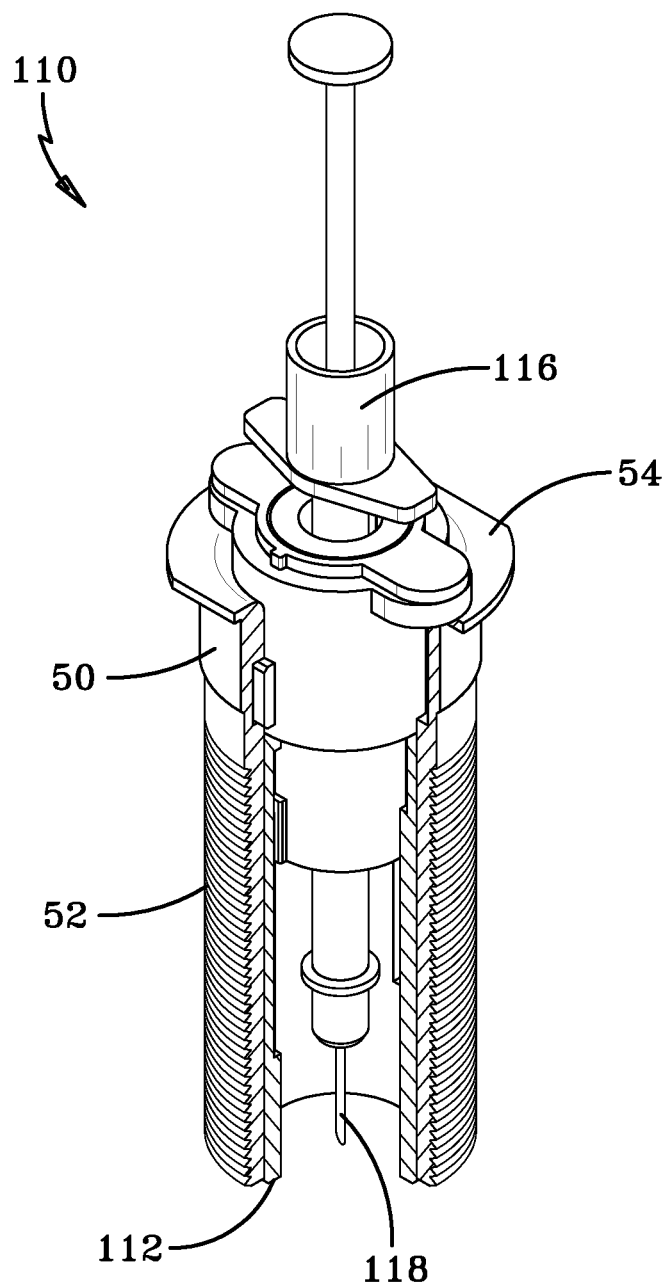
FIG. 10 is an exploded pictorial view of a subassembly of the exemplary device in combination with a syringe used for giving an injection.
Figure 12:
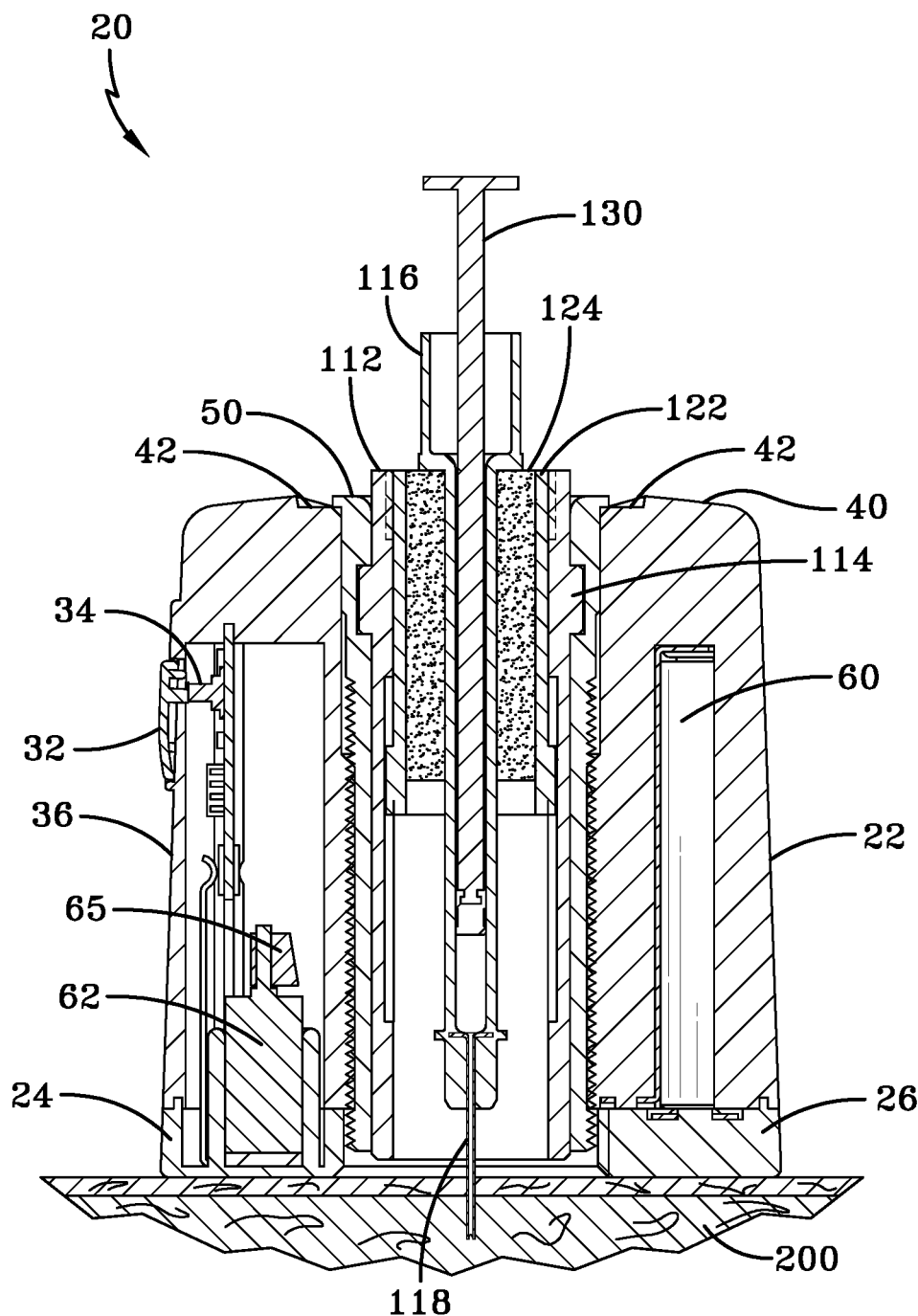
FIG. 12 is a section view of the exemplary device taken at line 12-12 of FIG. 9.
Figure 13:
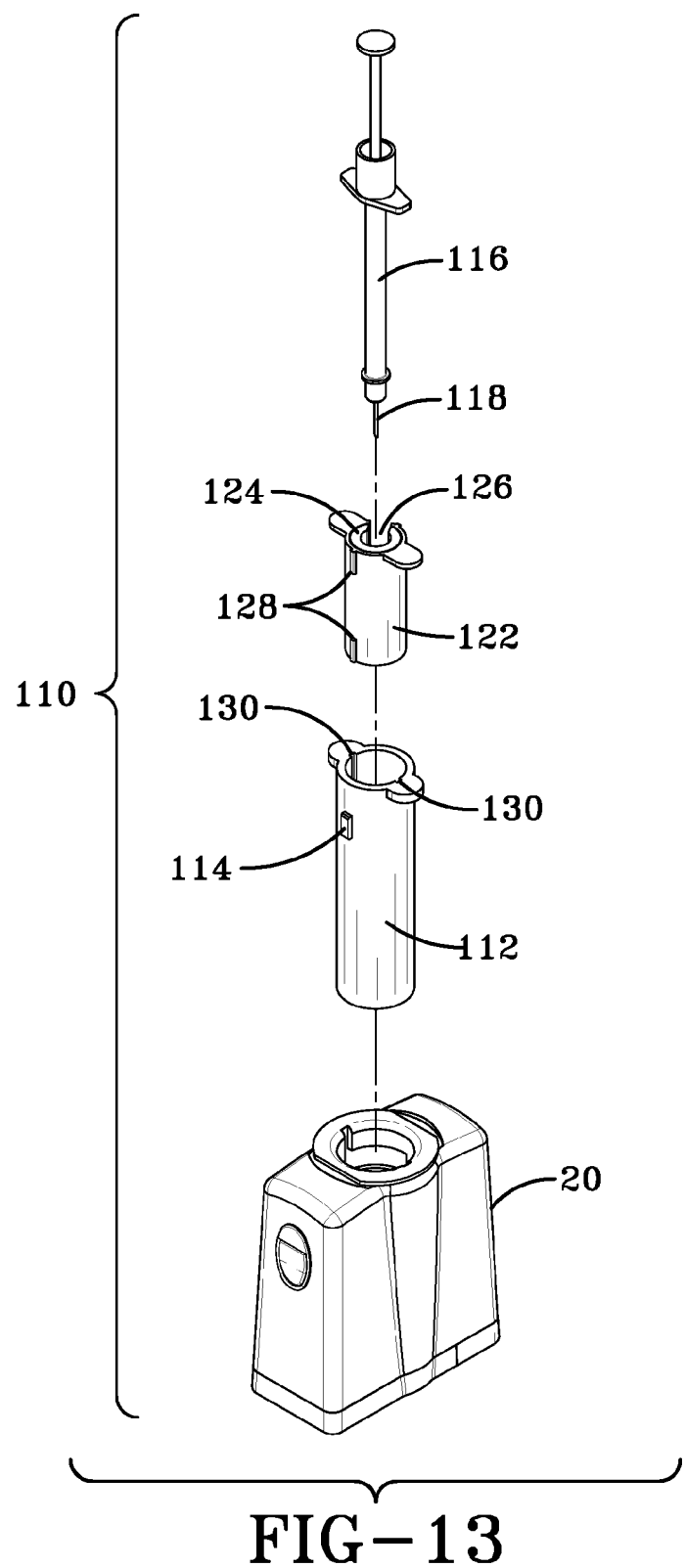
FIG. 13 is an exploded pictorial view showing the subassembly of FIG. 10.

The function of the injection assistance device of the present invention can be further explained with reference to FIGS. 8-13 in unison. FIG. 8 is a top perspective view and FIG. 9 is a bottom perspective view of the exemplary device in combination with a syringe used for giving an injection. FIG. 10 is an exploded pictorial view of a subassembly of the exemplary device in combination with a syringe used for giving an injection. FIG. 13 is an exploded pictorial view showing the subassembly of FIG. 10. FIG. 11 is a section view of the exemplary device taken at line 11-11 of FIG. 8. FIG. 12 is a section view of the exemplary device taken at line 12-12 of FIG. 9.

The exemplary device 20 is provided with an injection subassembly 110 that is shown separately in FIG. 10. In the example of the injection subassembly presented in the drawings a small insulin syringe 116 provided with a needle 118 is shown. It is to be understood that syringes and needles of a variety of sizes may be employed with the injection assistance device disclosed herein by varying the dimensions of components of the injection assistance device accordingly. The injection subassembly is shown assembled with the exemplary device in FIGS. 11 and 12. The threaded tubular insert 50 is normally first screwed into the housing body 22 as already described above using the threads 52 located on the threaded tubular insert. A tubular plastic insert 112 is inserted into the threaded tubular insert 50 and locked in an operative position by placing a tab 114 located on the exterior of the insert into the grooves 55, 57 on the interior of the threaded tubular insert 50 (see FIGS. 5 and 6) and rotating the tubular plastic insert 112 to lock it in place. It is to be understood that depending upon the size of a syringe to be used with the device the dimensions, and even the presence, of the tubular plastic insert 112 may be varied in accordance with good engineering practices.

A syringe receiver 122 is a plastic tubular member that contains a tubular foam insert 124 that receives the barrel of the syringe. If desired the syringe receiver 122 and the tubular foam member may be provided with aligned longitudinal slits 126 to facilitate snapping the syringe into the syringe receiver and foam insert before placing the syringe receiver/syringe assembly into the tubular plastic insert 112. However, if desired by a user the syringe receiver and foam insert alone may be inserted into the tubular plastic insert 112 and thereafter the syringe and needle may be inserted through the foam insert. It is recommended that the protective cap on the needle remain attached to the syringe during this procedure and then removed just prior to beginning the injection process. Tabs 128 in an exterior surface of the syringe receiver 122 are aligned with and slide in a longitudinal groove 130 in an interior surface of the tubular plastic insert 112 to restrict rotation of the syringe receiver, foam and syringe in the injection assistance device.

Perspective views of the injection assistance device 20 assembled with a syringe are shown in FIGS. 8 and 9. A user of the injection assistance device may turn on the DC electric motor 62 using the on/off switch 32 either before or after placing the lower surface of the injection assistance device comprising the housing cover 24 and battery compartment cover 26, against the skin of a person who is to receive an injection. The vibration of the lower surface of the injection assistance device against the skin of the person who is to receive an injection tends to distract the person from the invasive action of the needle used to deliver the injection. At that time the needle 18 as shown in FIG. 11 has not yet penetrated the skin of the person who is to receive the injection. The person administering the injection then depresses the syringe and needle to penetrate the skin of the person receiving an injection and thereafter depresses the plunger 130 of the syringe to cause the liquid, such as an insulin containing solution, to enter the person receiving the injection as shown in FIG. 12. After the administration of the injection is completed the needle is withdrawn and the injection assistance device 20 is removed from contact with the skin of the person who has received the injection.

It is not desirable for the needle and syringe to be vibrating during the insertion of the needle in a patient and the delivery of the medication. Such vibration of the needle would cause unnecessary discomfort and pain to the patient. The injection assistance device of the present invention prevents the vibration generated the DC electric motor from being transmitted to the syringe and needle through the use of an intervening foam insert 124 disposed intermediate the housing 22 of the injection assistance device and the syringe. In an exemplary prototype device for giving injections according to the present invention the plastic tubular syringe receiver 122 had an internal diameter of ⅜ inch and a small insulin syringe 116 had an outside diameter of ⅛ inch. The foam insert 124 had a thickness as measured perpendicular to a longitudinal axis of the plastic tubular syringe receiver 122 of about 3/16 inch, but in any case not greater than ¼ inch.

It has been found through experimentation that the foam tubular foam insert 124 must comprise a foam rigid enough to hold the syringe in place and yet flexible enough to arrest isolate all vibration occurring in other parts of the injection assistance device from the syringe and needle. It was found through experimentation that a polyurethane foam characterized by a particular hardness, namely an indentation force deflection of 25% at 127 N and 65% at 256N with an indentation ratio of 2.8 meets the criteria in the preceding sentence. Put another way the tubular foam insert 124 should comprise a foam having an ILD or IFD number greater than about 25% at 127 N and 65% at 256N with an indentation ratio of 2.8. ILD or IFD is an industry recognized measurement of firmness of how hard or soft a foam is. "ILD" stands for "indentation load deflection." "IFD" stands for "Indentation Force Deflection and the actual test method is basically identical to the older ILD test. The higher the ILD or IFD number of a foam is the firmer the foam is. The ILD or IFD number of a foam also represents how the force the foam will hold before it collapses. The polyurethane film used in a prototype was manufactured by Shenzhen Guozhihuifu Polymer Material Company Ltd., Xu Fei Garden, Building C, Room 1209, 2 Ba Guea Road, Fu Tian, Shenzhen, 518000, China.

The effectiveness of a tubular foam insert 124 in isolating a syringe and needle from the vibration of the housing of the device can be tested by having the needle project beyond the bottom of the housing, as it would when giving an injection, activating the motor to cause the housing to vibrate and then inserting the needle into a container of water. When the tubular foam insert comprised foam of the type specified in the preceding paragraph no ripples were seen in the water. When the tubular foam insert comprised foam comprised foams that were harder than the type specified in the preceding paragraph ripples appeared in the water.

It will be seen that the advantages set forth above, and those made apparent from the foregoing description, are efficiently attained and since certain changes may be made in the above construction without departing from the scope of the invention. It is intended that all matters contained in the foregoing description or shown in the accompanying drawings shall be interpreted as illustrative and not in a limiting sense. It is also to be understood that the following claims are intended to cover all of the generic and specific features of the invention herein described, and all statements of the scope of the invention which, as a matter of language, might be said to fall there between.

What is claimed is:

1. A device for giving injections comprising: a housing having a lower surface and an upper surface with a passage through the housing extending between the upper and lower surfaces; a DC motor with an eccentric weight fixed to the motor is located inside the housing to vibrate the housing; at least one tubular insert is located in the passage through the housing and is fixed to the housing; a syringe receiver is located inside and fixed to the at least one tubular insert with the syringe receiver containing a foam insert defining a space for receiving a syringe, the foam insert comprising a polyurethane foam.

2. A device for giving injections comprising: a housing having a lower surface and an upper surface with a passage through the housing extending between the upper and lower surfaces; a DC motor with an eccentric weight fixed to the motor is located inside the housing to vibrate the housing; a first tubular insert is located in the passage through the housing and is fixed to the housing; a second tubular insert is located inside the first tubular insert and is fixed to the first tubular insert; a syringe receiver is located inside and fixed to the second tubular insert with the syringe receiver containing a foam insert defining a space for receiving a syringe, the foam insert comprising a polyurethane foam.

3. A device for giving injections comprising: a housing having a lower surface and an upper surface with a passage through the housing extending between the upper and lower surfaces; a DC motor with an eccentric weight fixed to the motor is located inside the housing to vibrate the housing; a tubular insert is located in the passage through the housing and is fixed to the housing; a syringe receiver is located inside and fixed to the tubular insert with the syringe receiver containing a foam insert defining a space for receiving a syringe, the foam insert comprising a polyurethane foam.

* * * * *